US00PP08769P

United States Patent [19]

Van Der Jagt

[11] Patent Number: Plant 8,769

[45] Date of Patent: Jun. 7, 1994

[54] CHRYSANTHEMUM NAMED ORANGE REAGAN

[75] Inventor: Martinus Van Der Jagt, CJ Langeraar, Netherlands

[73] Assignee: Chrysanthemum Breeders Association, N.V., Netherlands Antilles

[21] Appl. No.: 780,237

[22] Filed: Oct. 22, 1991

[51] Int. Cl.[5] ..... A01H 5/00

[52] U.S. Cl. ..... Plt./82.3

[58] Field of Search ..... Plt. 74.1, 82.2, 82.3

[56] References Cited

PUBLICATIONS

Datta, 1991, "Evaluation of Recurrent Irradiation on Vegetatively Propagated Ornamentals: Chrysanthemum", J. Nuclear Agric. Biol., 20(2):81-86.

Banerji, et al., 1990, "Induction of Somatic Mutation in Chrysanthemum Cultivar 'Anupam'", J. Nuclear Agric. Biol., 19:252-256.

"Mutation Studies on Chrysanthemum." NBRI Newsletter 1989. 16(1):2-3.

Gosling, ed., 1979, "The Chrysanthemum Manual-6th Edition", The National Chrysanthemum Society, London, Essex Telegraph Press, Ltd., pp. 329-336.

Broertjes, et al., 1978, "Application of Mutation Breeding Methods in the Improvement of Vegetatively Propagated Crops", Elsevier Sci. Pub. Co., New York, pp. 162-175.

Gupta et al., 1978, "Mutation Breeding of Chrysanthemum. II Detection of Gamma Ray Induced Mutations in $vM_2$." J. Nuclear Agric. Biol. 7(2):50-54.

Das, et al., 1977, "Improvement of Some Vegetatively Propagated Ornamentals by Gamma Radiation", Indian J. Hort. 34(2):169-174.

Searle, et al., 1968, "Chrysanthemums the Year Round", Blanford Press, London, pp. 27-29, 320-327.

Broertjes, 1966, "Mutation Breeding of Chrysanthemums", Euphytica 15: 156-162.

Dowrick, et al., 1966, "The Induction of Mutation in Chrysanthemum Using X- and Gamma Radiation", Euphytica, 15:204-210.

*Primary Examiner*—Howard J. Locker

*Attorney, Agent, or Firm*—Parkhurst, Wendel & Rossi

[57] ABSTRACT

A new and distinct cultivar of Chrysanthemum plant named Orange Reagan, bearing medium sized orange blooms with a yellow-green center and a performance of 24-28 days.

2 Drawing Sheets

The present application is related to the following co-pending applications:

| Application No. | Filing Date | Title |
|---|---|---|
| 07/780,305 | October 22, 1991 | Reagan |
| 07/780,304 | October 22, 1991 | Salmon Reagan |
| 07/780,332 | October 22, 1991 | Dark Reagan (now abandoned and refiled on July 08, 1993, as continuing application Ser. No. 08/088104) |
| 07/780,292 | October 22, 1991 | Coral Reagan |
| 07/767,791 | September 30, 1991 | Sulfur Reagan (now abandoned and refiled on July 19, 1993, as continuing application Ser. No. 08/092942) |
| 07/767,881 | September 30, 1991 | Yellow Reagan |
| 07/780,238 | October 22, 1991 | Bronze Reagan (now abandoned and refiled on July 19, 1993, as continuing application Ser. No. 08/092941) |
| 07/780,233 | October 22, 1991 | White Reagan (now abandoned and refiled on July 08, 1993, as continuing application Ser. No. 08/088107) |

ORIGIN AND HISTORY OF THE NEW PLANT

The new plant of the present invention comprises a new and distinct cultivar of Chrysanthemum plant which is an induced mutation by gamma irradiation of a chrysanthemum named Reagan, which in turn is a cross of unknown *Chrysanthemum morifolium* parents. The chrysanthemum named Reagan is described in U.S. patent application Ser. No. 07/780,305. The invention was discovered by Martinus van der Jagt, Langeraarseweg 161F, 2461 CJ Langeraar, Holland in 1988. The invention has been asexually reproduced by cuttings in greenhouses at Ter Aar, Holland. The new cultivar has been found to retain its distinctive characteristics through successive propagations.

SUMMARY OF THE NEW PLANT

The present invention is a new and distinct variety of chrysanthemum of a medium sized bloom and orange color.

BRIEF DESCRIPTION OF THE DRAWINGS

The present new and distinct Chrysanthemum cultivar is shown in the accompanying drawings, the color being as nearly true as possible with color photographs of this type.

Sheet 1 shows the full bloom of the new cultivar;

Sheet 2, top, shows various stages of bloom of the new cultivar; and

Sheet 2, bottom, shows the foliage and petiole of the new cultivar.

DESCRIPTION OF THE INVENTION

This new variety of Chrysanthemum is of the botanical classification *Chrysanthemum morifolium,* and is named Orange Reagan. When grown in the vicinity of Ter Aar, Holland, it has a response time of approximately 7½ weeks. This new variety produces medium sized orange blooms with a yellow green center having a 4 week performance (i.e., a Vase life of 24–28 days). This new variety of Chrysanthemum has been found to retain its distinctive characteristics throughout successive propagations and may be planted under greenhouse conditions in Holland between weeks fifty and thirty-five (i.e., between December 1 and August 30). Pest resistance, disease resistance and frost tolerance are unknown.

Three groups consisting of 300, 300 and 400 cuttings, respectively, of the parent Reagan chrysanthemum were irradiated at 1250, 1500 and 1750 RAD, respectively. The cultivar of the present application was taken from the second group.

The following is a description of the plant and characteristics (color designations are from R.H.S. Color Chart) that distinguish it over related known varieties and its antecedents:

Botanical classification: *Chrysanthemum morifolium.*

Bud:

*Size.*—Medium (Cross section±1.0 cm, Height±0.7 cm.

*Form.*—Round and flat.

*Outside color.*—Greyed-Red 180 A.

Bloom:

*Size.*—Medium

*Fully expanded.*—7–7½ cm.

*Borne.*—Upper portion, single flower per peduncle; lower portion, plural flowers per peduncle.

*Stems.*—Strong, thick.

*Forms.*—Single (daisy).

*Performanence.*—Very good 24–28 Days (18°–20° C.).

Color:

*Center of flower.*—Immature: Yellow Green 151 C. Mature: Yellow Green 154 A.

*Base of petals.*—Between Greyed Orange 169A and B.

*Inside of petals.*—Between Greyed Orange 169A and B.

*Reverse of petals.*—Nearest to greyed-orange 163B tinged with red between the ribs.

*Outer petals.*—Between Greyed-Orange 169A and B.

*Tonality from a distance.*—An orange daisy with a fresh looking center having little or no pollen.

*Discoloration.*—Some to yellow orange 20 B.

*Pollen.*—Yellow-orange 14A.

Petals:

*Texture.*—Upperside smooth, underside smooth.

*Number.*—24–30 (Two rows).

*Cross-section.*—Convex.

*Arrangements.*—Imbricated.

*Persistence.*—Good. Petals keep straight or reflex somewhat at the edge at the end of blooming.

*Fragrance.*—Typical Chrysanthemum.

*Disc diameter.*—1.5 cm.

Reproductive organs:

*Stamen.*—Yellow, thick, 3 mm in length.

*Pollen.*—Appears at a late stage of blooming yellow orange in color.

*Styles.*—Green thick.

*Length.*—±5 mm.

*Stigmas.*—Yellow.

*Width.*—±1 mm.

*Ovaries.*—Enclosed in calyx.

Plant:

*Form.*—Spray mum meant for erect culture. Herbaceous.

*Growth.*—Strong.

*Height.*—100–125 cm.

*Peduncle.*—Near the top±14 cm, near the middle±24 cm, near the bottom±28 cm.

*Internodes.*—3 cm.

*Flowering response.*—7½ Weeks.

Foliage:

*Color.*—Upperside green 137 A, underside 137 C.

*Size.*—Length±12 cm, Width±9 cm.

*Quantity.*—22–28.

*Shape.*—Lobed, see photograph.

*Texture.*—Upperside rough, underside smooth slightly hirsute.

*Ribs and veins.*—Ribs well developed, veins not so developed.

*Edge.*—Crenated.

Distinguishing characteristics of the Chrysanthemum of the Reagan family are summarized below in Tables IA and IB. Each of the titled Reagans having a color designation is an induced mutation by irradiation of Reagan.

Color designation set forth in the following Tables are from the R.H.S. Color Chart.

TABLE IA

| | TITLE | | |
|---|---|---|---|
| | REAGAN | WHITE REAGAN | CORAL REAGAN |
| BUD OUTSIDE COLOR | GREYED-PURPLE 186D BUT PALER | YELLOW 4D | GREYED-PURPLE 186A |
| CENTER OF FLOWER: | | | |
| IM-MATURE: | YELLOW-GREEN 151C | YELLOW-GREEN 151C | YELLOW-GREEN 151C |
| MATURE: | YELLOW-GREEN 154A | YELLOW-GREEN 154A | YELLOW-GREEN 154A |
| BASE OF PETALS | PURPLE 75B | WHITE 155D BUT WHITER AND BRIGHTER | GREYED-RED 179C BUT REDDER |
| INSIDE OF PETALS | PURPLE 75B | WHITE 155D BUT WHITER AND BRIGHTER | GREYED-RED 179C BUT REDDER |
| REVERSE OF PETALS | RED-PURPLE 69A BUT PALER | WHITE 155D BUT WHITER AND BRIGHTER | GREYED-YELLOW 162D TINGED WITH RED-PURPLE 71B BETWEEN RIBS AND MARGIN |
| OUTER PETALS | PURPLE 75B | WHITE 155D BUT WHITER AND BRIGHTER | GREYED-RED 179C BUT REDDER |
| PETAL CROSS-SECTION | FLAT | FLAT | FLAT |

| | TITLE | | |
|---|---|---|---|
| | DARK REAGAN | ORANGE REAGAN | BRONZE REAGAN |
| BUD OUTSIDE COLOR | BETWEEN GREYED PURPLE 186A AND B | GREYED-RED 180A | GREYED-RED 179C |
| CENTER OF | | | |

TABLE IA-continued

| | | | |
|---|---|---|---|
| FLOWER: | | | |
| IM-MATURE: | YELLOW-GREEN 151C | YELLOW-GREEN 151C | YELLOW-GREEN 151C |
| MATURE: | YELLOW-GREEN 154A | YELLOW-GREEN 154A | YELLOW-GREEN 154A |
| BASE OF PETALS | RED-PURPLE 69B LIGHTLY OVERLAID WITH RED-PURPLE 72A GIVING AN OVERALL IMPRESSION OF PURPLE 75A BUT PINKER | BETWEEN GREYED ORANGE 169A AND B | YELLOW 8A WITH AN OVERLAY OF GREYED RED 179B |
| INSIDE OF PETALS | RED-PURPLE 69B LIGHTLY OVERLAID WITH RED-PURPLE 72A GIVING AN OVERALL IMPRESSION OF PURPLE 75A BUT PINKER | BETWEEN GREYED ORANGE 169A AND B | YELLOW 8A WITH AN OVERLAY OF GREYED RED 179B |
| REVERSE OF PETALS | RED-PURPLE 69C WITH A LIGHT TES-SELLATION OF RED-PURPLE 72A | NEAREST TO GREYED-ORANGE 163B TINGED WITH RED BETWEEN THE RIBS | YELLOW 8C TINGED ALONG THE CENTER WITH GREYED RED 179B IN A TESSEL-LATED PATTERN |
| OUTER PETALS | RED-PURPLE 69B LIGHTLY OVERLAID WITH RED-PURPLE 72A GIVING AN OVERALL IMPRESSION OF PURPLE 75A BUT PINKER | BETWEEN GREYED-ORANGE 169A AND B | YELLOW 8A WITH AN OVERLAY OF GREYED RED 179B |
| PETAL CROSS-SECTION | CONVEX | CONVEX | FLAT |

| | TITLE | | |
|---|---|---|---|
| | YELLOW REAGAN | SULPHUR REAGAN | SALMON REAGAN |
| BUD OUTSIDE COLOR CENTER OF FLOWER: | YELLOW 9C | YELLOW 10C | NEAREST TO YELLOW-ORANGE 23D |
| IM-MATURE: | YELLOW-GREEN 151C | YELLOW-GREEN 151C | YELLOW-GREEN 151C |
| MATURE: | YELLOW-GREEN 154A | YELLOW-GREEN 154A | YELLOW-GREEN 154A |
| BASE OF PETALS | YELLOW 5C | YELLOW 6D | NEAREST TO ORANGE 29C |
| INSIDE OF PETALS | YELLOW 5C | YELLOW 6D | NEAREST TO ORANGE 29C |
| REVERSE OF PETALS | YELLOW 4C | YELLOW 6D | NEAREST TO YELLOW-ORANGE 22D |
| OUTER PETALS | YELLOW 5C | YELLOW 6D | NEAREST TO ORANGE 29C |
| PETAL CROSS-SECTION | FLAT | FLAT | FLAT |

TABLE IB

| | TITLE | |
|---|---|---|
| | REAGAN | WHITE REAGAN |
| STEM INFORMATION | | |
| STEM: GREEN COLOR | YELLOW-GREEN 144A | NEAREST GREEN 143C |
| STEM: ANTHOCYANIN COLORATION | ABSENT | ABSENT |
| STEM: STRENGTH | MEDIUM | MEDIUM TO STRONG |
| STEM: BRITTLENESS | PRESENT | PRESENT |
| PEDUNCLE INFORMATION | | |
| LATERAL SHOOT: ATTACHMENT TO STEM | MEDIUM | WEAK TO MEDIUM |
| LATERAL SHOOT: ANGLE BETWEEN LATERAL SHOOT AND STEM | MEDIUM | MEDIUM |
| ADDITIONAL FOLIAGE INFORMATION | | |
| LEAF: SHAPE OF BASE OF SINUS BETWEEN LATERAL LOBES | ROUND | ROUND |
| LEAF: MARGINS OF SINUS BETWEEN LATERAL LOBES | CONVERGING | CONVERGING |
| LEAF: SHAPE OF BASE | ROUNDED | ASYMMETRIC |
| LEAF: APEX | CUSPIDATE | MUCRONATE |
| GROWTH: | | |
| DIFFERENCE IN AVERAGE LENGTH (IN CMS) | | |
| | 0 | 0 |
| RESPONSE TIME: | | |
| DIFFERENCE IN DAYS OF AVERAGE RESPONSE | | |
| | 0 | 0 |
| RESPONSE ON ALAR: DOSE THAT HAS TO BE USED TO GET AN AVERAGE LENGTH OF ABOUT 90 CMS (DOSE IN GRAMS PER 100 LITER OF WATER) | | |
| | 300 | 300 |
| YEAR OF DISCOVERY | 1986 | 1989 |

| | TITLE | |
|---|---|---|
| | CORAL REAGAN | DARK REAGAN |
| STEM INFORMATION | | |
| STEM: GREEN COLOR | YELLOW-GREEN 144A | YELLOW-GREEN 144A |
| STEM: ANTHOCYANIN COLORATION | PRESENT | PRESENT |
| STEM: STRENGTH | MEDIUM | MEDIUM |
| STEM: BRITTLENESS | ABSENT | PRESENT |
| PEDUNCLE INFORMATION | | |
| LATERAL SHOOT: ATTACHMENT TO STEM | WEAK TO MEDIUM | MEDIUM |
| LATERAL SHOOT: ANGLE BETWEEN LATERAL SHOOT AND STEM | SMALL | MEDIUM |
| ADDITIONAL FOLIAGE INFORMATION | | |
| LEAF: SHAPE OF BASE OF SINUS BETWEEN LATERAL LOBES | ROUND | ROUND |
| LEAF: MARGINS OF SINUS BETWEEN LATERAL LOBES | CONVERGING | CONVERGING |
| LEAF: SHAPE OF BASE | ASYMMETRIC | ASYMMETRIC |
| LEAF: APEX | CUSPIDATE | MUCRONATE |
| GROWTH: | | |
| DIFFERENCE IN AVERAGE LENGTH (IN CMS) | | |
| | −5 | 0 |
| RESPONSE TIME: | | |
| DIFFERENCE IN DAYS OF AVERAGE RESPONSE | | |
| | +1 | +½ |

TABLE IB-continued

| | | |
|---|---|---|
| RESPONSE ON ALAR: DOSE THAT HAS TO BE USED TO GET AN AVERAGE LENGTH OF ABOUT 90 CMS (DOSE IN GRAMS PER 100 LITER OF WATER) | | |
| | 250 | 300 |
| YEAR OF DISCOVERY | 1988 | 1988 |
| | TITLE | |
| | ORANGE REAGAN | BRONZE REAGAN |
| STEM INFORMATION | | |
| STEM: GREEN COLOR | BETWEEN YELLOW-GREEN 144A AND 146B | YELLOW-GREEN 144A |
| STEM: ANTHOCYANIN COLORATION | PRESENT | PRESENT |
| STEM: STRENGTH | MEDIUM | MEDIUM |
| STEM: BRITTLENESS | PRESENT | ABSENT |
| PEDUNCLE INFORMATION | | |
| LATERAL SHOOT: ATTACHMENT TO STEM | MEDIUM | WEAK |
| LATERAL SHOOT: ANGLE BETWEEN LATERAL SHOOT AND STEM | SMALL | SMALL |
| ADDITIONAL FOLIAGE INFORMATION | | |
| LEAF: SHAPE OF BASE OF SINUS BETWEEN LATERAL LOBES | ROUND | ROUND |
| LEAF: MARGINS OF SINUS BETWEEN LATERAL LOBES | CONVERGING | CONVERGING |
| LEAF: SHAPE OF BASE | TRUNCATE | ASYMMETRIC |
| LEAF: APEX | CUSPIDATE | CUSPIDATE |
| GROWTH: DIFFERENCE IN AVERAGE LENGTH (IN CMS) | | |
| | +10 | 0 |
| RESPONSE TIME: DIFFERENCE IN DAYS OF AVERAGE RESPONSE | | |
| | −1 | −½ |
| RESPONSE ON ALAR: DOSE THAT HAS TO BE USED TO GET AN AVERAGE LENGTH OF ABOUT 90 CMS (DOSE IN GRAMS PER 100 LITER OF WATER) | | |
| | 450 | 250 |
| YEAR OF DISCOVERY | 1988 | 1988 |
| | TITLE | |
| | YELLOW REAGAN | SULPHUR REAGAN |
| STEM INFORMATION | | |
| STEM: GREEN COLOR | YELLOW-GREEN 146B | NEAREST GREEN 143C |
| STEM: ANTHOCYANIN COLORATION | ABSENT | ABSENT |
| STEM: STRENGTH | MEDIUM | MEDIUM TO STRONG |
| STEM: BRITTLENESS | ABSENT | ABSENT |
| PEDUNCLE INFORMATION | | |
| LATERAL SHOOT: ATTACHMENT TO STEM | WEAK TO MEDIUM | WEAK TO MEDIUM |
| LATERAL SHOOT: ANGLE BETWEEN LATERAL SHOOT AND STEM | SMALL | SMALL |

TABLE IB-continued

| | | |
|---|---|---|
| ADDITIONAL FOLIAGE INFORMATION | | |
| LEAF: SHAPE OF BASE OF SINUS BETWEEN LATERAL LOBES | ROUND | ROUND |
| LEAF: MARGINS OF SINUS BETWEEN LATERAL LOBES | PARALLEL | PARALLEL |
| LEAF: SHAPE OF BASE | ASYMMETRIC | ASYMMETRIC |
| LEAF: APEX | MUCRONATE | MUCRONATE |
| GROWTH: DIFFERENCE IN AVERAGE LENGTH (IN CMS) | | |
| | 0 | +10 |
| RESPONSE TIME: DIFFERENCE IN DAYS OF AVERAGE RESPONSE | | |
| | +1 | −1 |
| RESPONSE ON ALAR: DOSE THAT HAS TO BE USED TO GET AN AVERAGE LENGTH OF ABOUT 90 CMS (DOSE IN GRAMS PER 100 LITER OF WATER) | | |
| | 280 | 450 |
| YEAR OF DISCOVERY | 1990 | 1990 |
| | TITLE | |
| | SALMON REAGAN | |
| STEM INFORMATION | | |
| STEM: GREEN COLOR | YELLOW-GREEN 144A | |
| STEM: ANTHOCYANIN COLORATION | PRESENT | |
| STEM: STRENGTH | MEDIUM | |
| STEM: BRITTLENESS | PRESENT | |
| PEDUNCLE INFORMATION | | |
| LATERAL SHOOT: ATTACHMENT TO STEM | MEDIUM | |
| LATERAL SHOOT: ANGLE BETWEEN LATERAL SHOOT AND STEM | MEDIUM | |
| ADDITIONAL FOLIAGE INFORMATION | | |
| LEAF: SHAPE OF BASE OF SINUS BETWEEN LATERAL LOBES | ROUND | |
| LEAF: MARGINS OF SINUS BETWEEN LATERAL LOBES | PARALLEL | |
| LEAF: SHAPE OF BASE | ASYMMETRIC | |
| LEAF: APEX | CUSPIDATE | |
| GROWTH: DIFFERENCE IN AVERAGE LENGTH (IN CMS) | | |
| | +10 | |
| RESPONSE TIME: DIFFERENCE IN DAYS OF AVERAGE RESPONSE | | |
| | 0 | |
| RESPONSE ON ALAR: DOSE THAT HAS TO BE USED TO GET AN AVERAGE LENGTH OF ABOUT 90 CMS (DOSE IN GRAMS PER 100 LITER OF WATER) | | |
| | 350 | |
| YEAR OF DISCOVERY | 1987 | |

What is claimed is:

1. A new and distinct cultivar of chrysanthemum plant named Orange Reagan, as described and illustrated.

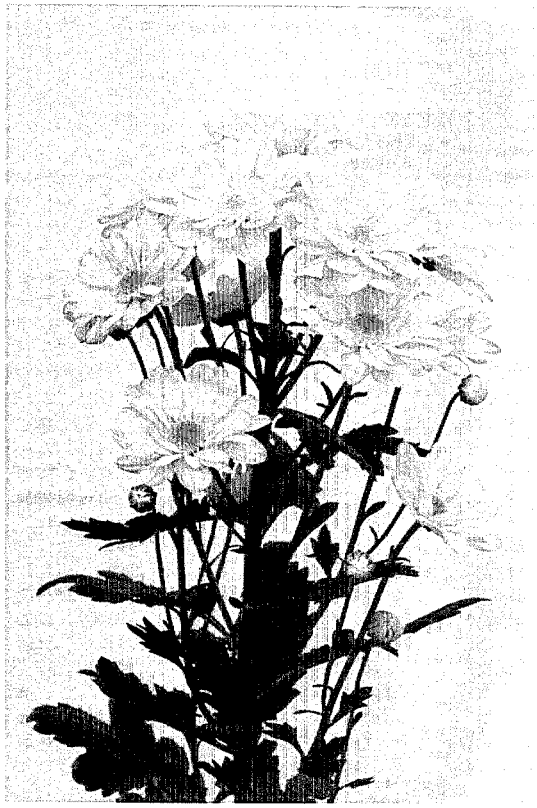

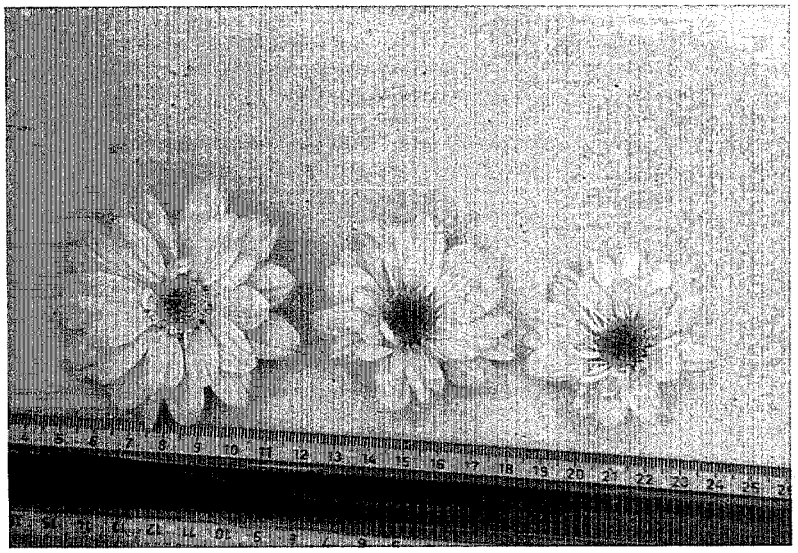
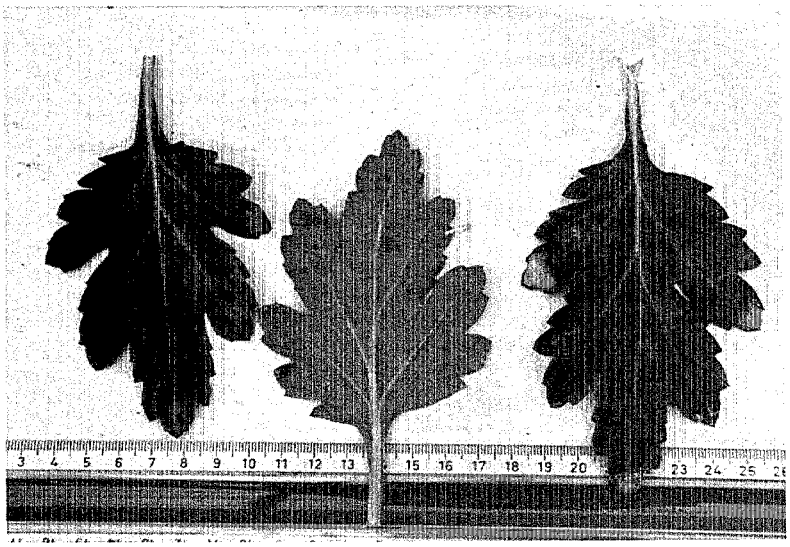

* * * * *